United States Patent [19]

Rullier et al.

[11] 4,202,592
[45] May 13, 1980

[54] SEALED ELECTRICAL CONNECTORS

[75] Inventors: Nöel Rullier, Clamart; Michel Benel, Fontenay-aux-Roses, both of France

[73] Assignee: Societe Anonyme dite: Ela Medical, France

[21] Appl. No.: 898,780

[22] Filed: Apr. 21, 1978

[30] Foreign Application Priority Data

May 6, 1977 [FR] France .................... 77 13816

[51] Int. Cl.² ............... A61N 1/36; H01R 13/54
[52] U.S. Cl. ............... 339/116 R; 128/419 P; 339/92 R
[58] Field of Search ........... 128/419 P, 419 PS, 421, 128/422; 339/61 R, 75 R, 92 R, 94, 263 R, 116 R, 116 C

[56] References Cited

U.S. PATENT DOCUMENTS

| 3,340,493 | 9/1967 | Fisher et al. ............ 339/61 R |
| 3,760,332 | 9/1973 | Berkovits et al. ....... 339/94 R X |
| 3,818,304 | 6/1974 | Hursen et al. .......... 128/419 PS X |
| 3,822,707 | 7/1974 | Adducci et al. ......... 128/419 PS X |

FOREIGN PATENT DOCUMENTS 1111347  4/1968  United Kingdom ............ 339/61 R

Primary Examiner—Roy Lake
Assistant Examiner—E. F. Desmond
Attorney, Agent, or Firm—Robert E. Burns; Emmanuel J. Lobato; Bruce L. Adams

[57] ABSTRACT

A sealed electrical connector comprises an electrically insulated pin housed in a receptacle and has a bared end for contact with a conductor extending partly out of the receptacle. An adjustable mechanical means is provided establishing such contact. A deformable resilient sleeve serves to seal the connection between the pin and receptacle, and access to the mechanical means is only possible through one end and along the sleeve which serves thus to seal the mechanical means.

The connector is suitable for use with an implantable cardiac stimulator.

12 Claims, 5 Drawing Figures

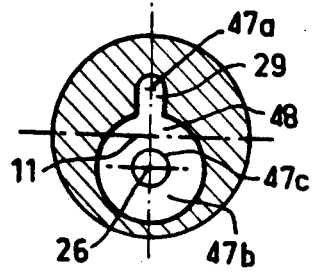
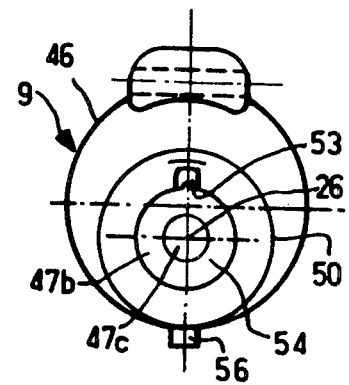
FIG. 4          FIG. 3
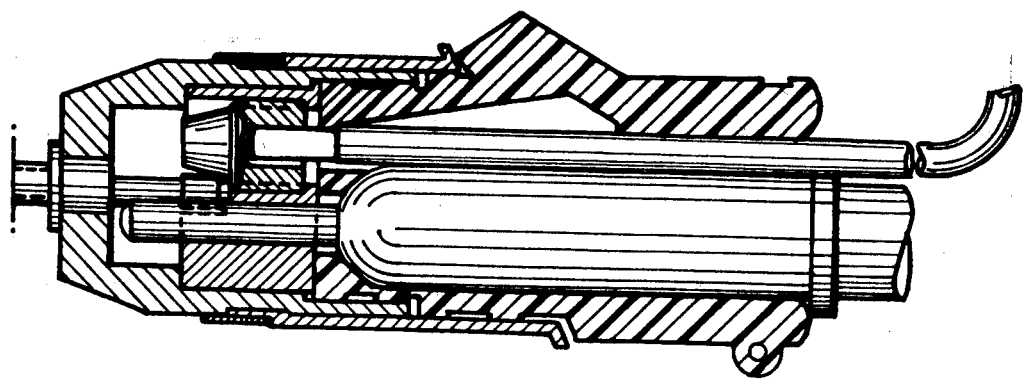
FIG. 5

SEALED ELECTRICAL CONNECTORS

The invention relates to a sealed electrical connector intended particularly, but not exclusively, for an implantable cardiac stimulator.

Implantable cardiac stimulators are already provided with sealed electrical connectors intended to receive an electrically insulated pin connected to a cardiac probe. These electrical connectors comprise a receptacle able to receive the pin, comprising means conducting electricity, mechanical means for locking the pin with respect to the receptacle, which means are removable and therefore accessible from outside the receptacle, means for sealing the connection of the pin and receptacle and means for sealing the mechanical locking means. By way of example, these mechanical locking means are in the form of a screw or the like mounted in a screw-thread in the receptacle having an axis subbstantially perpendicular to the axis of engagement of the pin in the receptacle.

These sealed electrical connectors known hitherto are not completely satisfactory in view of the fact that the receptacle comprises two openings, one for the pin, the other for gaining access to the means for locking the latter with respect to the receptacle, which openings are thus areas requiring sealing means and are always the cause of leakages.

Moreover, the tapped hole into which the screw for locking the pin is screwed, has a small size such that the tool intended to screw or unscrew this screw is not guided in its movement for gaining access to the mechanical locking means.

The present invention intends to remedy these various drawbacks and to this end proposes a sealed electrical connector in which the mechanical locking means are accessible solely by the opening through which the pin is engaged in the receptacle. In addition, this connector has no specific sealing means intended for the mechanical locking means. The latter are protected solely by the means sealing the connection of the pin and receptacle.

Other features of the invention will become apparent on reading the following description of a preferred but non-limiting embodiment of the invention, with reference to the accompanying drawings in which:

FIG. 3 is an elevational view of an insulating sleeve in the direction of arrow F of FIG. 2.

FIG. 4 is a sectional view on line IV—IV of FIG. 2 of the sleeve.

FIG. 5 is an axial sectional view showing the useful position of an operating tool.

Figure 1:
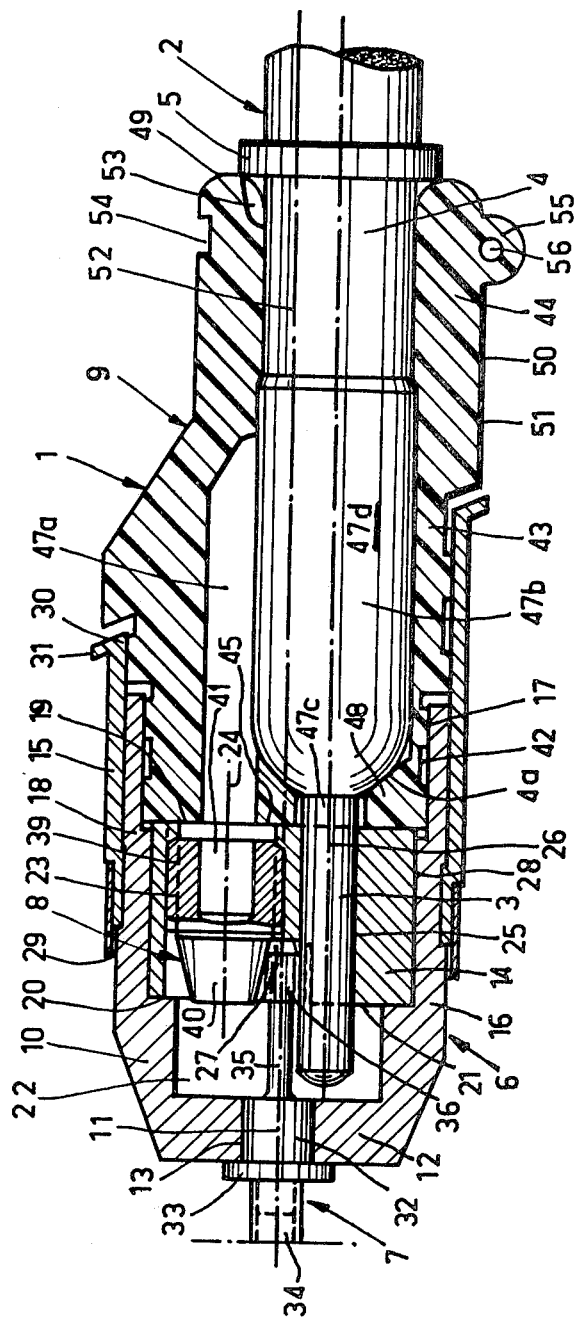
FIG. 1 is a longitudinal axial sectional view of a sealed electrical connector according to the invention in which a pin is engaged.
Figure 2:
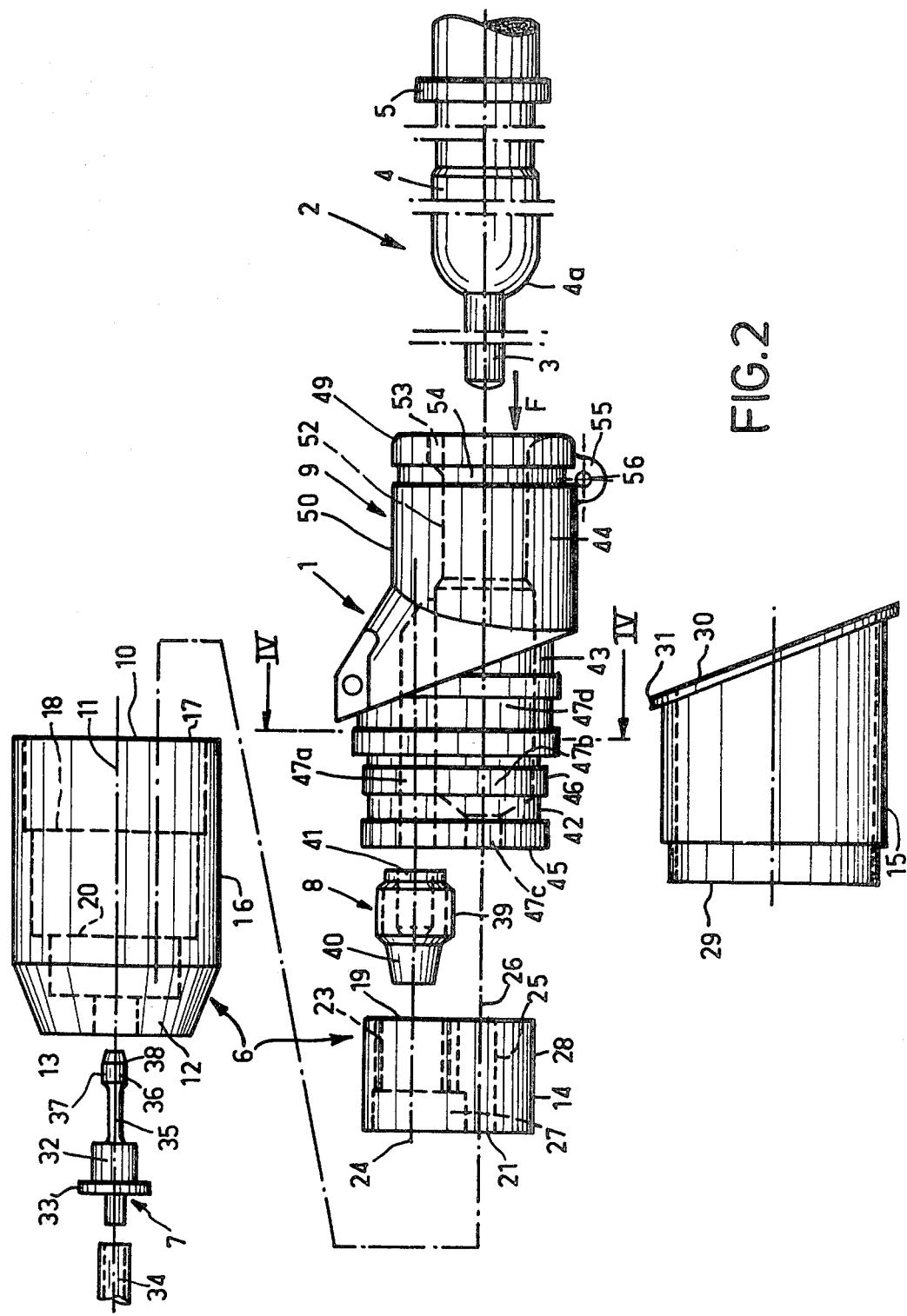
FIG. 2 is an exploded elevational view of the connector illustrated in FIG. 1 and of the pin.

The figures show a sealed electrical connector 1 according to the invention, connected for example, but not exclusively, to an implantable cardiac stimulator which is not shown, intended to receive an electrical pin 2, connected for example, but not exclusively, to a cardiac probe which is not shown.

The pin 2 comprises an electrical lead whereof an end part 3 is stripped and has a certain rigidity and an electrical insulating sheath 4 surrounding the lead with the exception of its stripped end part 3, for example of a substance having a certain elasticity such as an elastomer (in particular silicone). If necessary, the sheath 4 comprises a projection 5 for example in the form of a continuous flange, at an appropriate location determined subsequently.

The connector 1 comprises a receptacle 6 able to receive the pin 2, inside which are partly housed means 7 for conducting electricity, thus passing through this receptacle 6, mechanical means 8 for locking the pin 2 with respect to the receptacle 6, which means are removable and accessible from outside the receptacle 6 and sealing means and located between the receptacle 6 and the pin 2 to ensure the seal of the connection of the connector 1 and pin 2.

According to the invention and as will be described hereafter in detail, access to the mechanical locking means 8 is gained through the opening for the introduction of the pin 2 into the receptacle 6. In addition, the electrical connector 1 comprises no specific sealing means intended for the mechanical locking means 8. This function is fulfilled by the sealing means 9.

The receptacle 6 comprises a cup 10 of insulating material, having a shape of revolution about an axis 11, for example a cylindrical or partly cylindrical, partly frustoconical shape, whereof the base 12 is provided with a hole 13 along the axis 11 facilitating the passage of means 7 for conducting electricity, an insert 14 housed in the cup 10 and secured rigidly to the latter by any appropriate means, in particular by sticking, having a general cylindrical shape and finally, a rigid member 15 surrounding the cylindrical wall 16 of the cup 10, adjacent its outer face and its free circular edge 17 opposite the base 12, having a general cylindrical or pseudo-cylindrical shape.

Starting from its free edge 17 opposite the base 12, the inner face of the cylindrical wall 16 of the cup 10 comprises two successive shoulders or circumferential projections, namely a first shoulder 18, aligning at least substantially with the outer circular face 19 of the insert 14 directed towards the free edge 17 and a second shoulder 20, nearer the base 12, against which is pressed the edge of the inner circular face 21 of the insert 14, directed towards the base 12. Since the second shoulder 20 is at a distance from the base 12, the cup 10 comprises a cavity 22 defined by the base 12 and the inner circular face 21.

The first shoulder 18 is desirable but optional. As regards the second shoulder 20, it may be replaced by any other equivalent means facilitating correct positioning of the insert 14 with respect to the cup 10.

The insert 14 is made of metal for example and having a tapped hole 23 on the axis 24 and a smooth hole 25 on the axis 26, these two holes 23, 25 each opening out in the outer and inner circular faces 19 and 21 respectively and the two axes 24 and 26 being parallel to each other and at a distance apart. A blind hole 27 on the axis 11 cut in the insert 14 from its inner circular face 21 facilitates communication between the tapped hole 23 and smooth hole 25 over a certain distance.

The dimensions of the insert 14 are such that the latter is adapted to the dimensions of the cup 10 between the first and second shoulders 18, 20.

To facilitate connection of the insert 14 to the cup 10, by means of adhesive for example, one or more recesses in which the adhesive is placed may be provided for example on the inner face of the cylindrical wall 16 of the cup and/or on the corresponding outer cylindrical face 28 of the insert 14.

The member 15 is made of metal for example and is in the form of a sheath on the axis 11, defined by a free circular edge 29 located substantially in the central area of the outer face of the cylindrical wall 16 of the cup 10 and a second free edge 30 which is elliptical in the embodiment illustrated and comprising an outer lip 31. As shown in the drawings, the dimensions of the member 15 are such that the latter projects from the cup 10 from its free circular edge 17 as far as the elliptical edge 30. The member 15 is located correctly with respect to the cup 10 which it surrounds for example by means of a projection of the outer face of the cylindrical wall 16 of the cup 10 on which the free circular edge 29 of the member 15 bears. The member 15 and cup 10 are connected by any appropriate means, in particular by sticking or even by means of a securing collar, or by brazing etc.

The means 7 for conducting electricity comprise a member 32, housed in the hole 13 in the cup 10 and fixed to the latter by any appropriate means, in particular through the intermediary of an outer flange 33 extended towards the outside of the cup 10 by a connecting member 34 and, towards the inside of the cup by a stem 35 which conducts electricity, having a certain rigidity but which is able to be slightly deformed elastically with respect to its normal inoperative position along the axis 11, owing to the existence of the cavity 22, terminated at its free end part by an electrical contact member 36, housed in the blind hole 27 in the insert 14.

In a preferred embodiment of the invention, the axes 11, 24 and 26 are coplanar and the member 36 is limited adjacent the tapped hole 23 and the smooth hole 25 respectively by two surfaces 37, 38 which are flat and substantially perpendicular to the plane defined by the axes 11, 24, 26. More precisely, the surfaces 37 and 38 may at least partly complement the corresponding contacting surfaces on the one hand of the member for locking the connector and on the other hand of the stripped end part 3 of the pin 2.

The mechanical locking means 8 are in the form of a member comprising a screw-threaded part 39 cooperating with the tapped hole 23 of the insert 14, extended in the direction of the base 12 of the cup 10 by a locking part 40 of general frustoconical shape whose major base is adjacent the screw-threaded part 39 and whose minor base is directed towards the base 12. Adjacent the outer circular face 19 of the insert 14, the part 39 comprises gripping means 41 making it possible to pivot the part 8 about the axis 24, in the tapped hole 23, in either direction.

In a preferred but non-limiting embodiment, these gripping means 41 are in the form of a blind hole having a cross section complementing that of a tool which is not shown. In particular, this blind hole may have a polygonal, in particular hexagonal cross section.

It is apparent from the preceding description that the locking means 8 are accessible solely through the opening provided in the outer circular face 19 of the insert 14 communicating with the tapped hole 13.

The sealing means 9 have a quadruple function: the first is to guide and limit the movement of the pin; the second is to seal the connection of the pin and connector; the third is to guide the tool making it possible to operate the mechanical locking means 8 and the fourth is to seal the connector taking into account the existence of mechanical locking means 8.

These four functions are fulfilled by the means 9 in the form of a sleeve of general pseudo-cylindrical shape, made of elastically deformable material, in particular an elastomer, such as silicone, rigidly secured to the receptacle 6, in particular the cup 10 and the member 15, by any appropriate means, in particular sticking.

The sleeve 9 comprises an inner end part 42 adjacent the insert 14 and housed in the cup 10, a central part 43 adjacent the part 42, partly housed in the member 15 and an outer end part 44, adjacent the central part 43, located outside the member 15.

The inner end part 42 is defined externally by an inner circular front face 45 located in the same plane as the outer circular face 19 of the insert 14 and a cylindrical or pseudo-cylindrical face 46 pressed on the inner faces of the cylindrical wall 16 of the cup 10 and on the inner face of the member 15. The cylindrical face 46 thus has a shape at least partly complementing that of these two faces. The sleeve 9 is connected to the cup 10 and/or the member 15 by any appropriate means, in particular by sticking. To this end, hollows or grooves in which adhesive may be placed are provided in the cup 10 and/or in the member 15 and/or in the outer cylindrical face 46.

A through-hole 47 is provided in the inner part 42, which hole is formed by the combination of a first hole 47a on the axis 24, having a diameter smaller than that of the tapped hole 23 and larger than that of the blind hole constituting the gripping means 41 and of a second hole on the axis 26, itself comprising a first restricted section 47c adjacent the front face 45 and having a diameter substantially equal to that of the hole 25, separated from the first hole 47a by a projection 48 and a second enlarged section 47d communicating with the first hole 47a and in which the sheath 4 for the electrical insulation of the pin 2 may be housed.

Adjacent its free end opposite the front face 45, the projection 48 on the axis 26 has a shape at least partly complementing that of the free end part 4a of the insulating sheath 4 adjacent the stripped part 3. In particular, the free end part 4a may be in the form of a spherical sector. The contact of this part 4a and the projection 48 makes it possible to limit the movement of the pin 2 in the direction of the base 12.

The outer end part 44 is in the form of a sleeve on the axis 26, limited externally by a circular outer front face 49 and a cylindrical or pseudo-cylindrical face 50 having a generatrix 51 located for example substantially in the extension of the outer face of the member 15 at the point of the elliptical edge 30 furthest from the base 12. This part 44 is provided with a through-hole 52 on the axis 26, normally having a diameter at least partly less than the outer diameter of the sheath 4 in its normal state. A slot 53 located on the axis 24 and cut in the part 44 is adjacent the front face 49 on the one hand and the hole 52 on the other hand. This slot 53 which does not extend over the entire length of the hole 52 serves as a guide for a tool for actuating the mechanical locking means 8.

An outer groove 54 in the outer cylindrical face 50 and a projecting lug 55 adjacent the groove 54, provided with a hole 56 are also preferably provided. A wire may be placed in the hole 56 and the groove 54 and clamp the end part 44 against the insulation sheath 4. It should be noted that owing to the respective dimensions of the hole 52 and the insulation sheath 4, the outer end part 44 normally clamps the insulation sheath 4 elastically over the entire length of the hole 52, which is sufficient to ensure a seal between the pin 2 and the connector 1.

The central part 43 connects the end parts 42 and 44 which are off-centre one with respect to the other, as has been shown. This central part 43 thus has an appropriate shape and also comprises a recess 57 of general elliptical shape co-operating with the outer lip 31 of the member 15.

Internally, the central part 43 is provided with a hole corresponding to the extension of the second enlarged section 47d and with the first hole 47a which is blind at the junction point of the central part 53 and the outer end part 44, as shown in the drawings.

The operation of the connector which has been described is as follows:

The pin 2 is introduced by its stripped end part 3 into the connector 1 through the opening of the hole 52 located in the outer front face 49 of the sleeve 9. This introduction is facilitated owing to the fact that the outer diameter of the stripped end part 3 is less than the inner diameter of the hole 52. This movement may be continued until the free end part 4a of the sheath 4 comes into contact with the front face 49. Owing to the shape of this free end part 4a, it is possible to insert the insulation sheath 4 in the hole and then to slide the latter by deforming the outer end part 44 of the sleeve 9 elastically, in view of the fact that the normal inner diameter of the hole 52 is less than the normal outer diameter of the sheath 4. The movement may be continued, the stripped end part 3 passing through the second enlarged section 47d then the first restricted section 47c, then subsequently, the smooth hole 25 located in the extension of the first restricted section 47c, then finally the cavity 22 until the free end part 4a is locked against the projection 48. This sliding of the stripped end part 3 is not hindered by the existence of the electrical contact member 36, in view of the location of the latter with respect to the smooth hole 25 and the shape of the surface 38.

In the correct position of the pin 2, the projection 5 of this pin comes into contact with the front end face 49.

In order to connect the pin 2 securely to the connector 1, a tool for actuating the mechanical locking means 8 is introduced into the latter. This tool which is not part of the present invention is in the form of a spanner of sufficient length, whose shape is able to co-operate with the gripping means 41. The tool is placed firstly in the slot 53 of appropriate shape. The tool is then pushed towards the inside of the connector 1 and this movement is made possible by an elastic deformation of the outer end part 44 which is moved away from the insulation sheath 4 in the extension of the hole 47a. The movement is continued until the tool reaches the extension of the first hole 47a of the central part 43, then the first hole 47a in the inner part 42. The existence of this hole thus makes it possible to guide the tool in its movement such that the tool naturally reaches the successive gripping means 41 owing to the tapped hole 23 provided in the insert 14. By pivoting the tool, it is possible to move the screw-threaded part 39 of the means 8, thus the adjacent locking part 40. Since the latter is in the shape of a truncated cone, it comes to bear and slide on the surface 37 of the electrical contact part 36, causing its movement by elastic deformation of the stem 35 until the surface 38 comes into contact with the corresponding surface of the stripped end part 3, which produces an electrical contact between these two parts (FIG. 5).

It is then possible to withdraw the tool for actuating the locking means 8 of the connector. The outer end part 44 is thus once more pressed elastically against the insulation sheath 4.

To obtain a better seal, it is possible to use a wire passing through the groove 54 and the hole 56 in the lug 55, as already mentioned.

It is clear that it is possible to extract the pin 2 from the connector by reversing the operations which have been described.

What is claimed is:

1. A sealed electrical connector, especially for use with an implantable cardiac stimulator, comprising an electrically insulated pin having a stripped end, a receptacle receiving said end of said pin, means for conducting electricity from said pin, mechanical means for locking said pin with respect to said receptacle, said mechanical locking means comprising a screw engaging in a tapped hole in said receptacle, the axis of said tapped hole being parallel to an axis along which said pin slides with respect to said connector, and means for sealing the connection between said pin and said receptacle, said sealing means having an opening through which said pin is engaged in said connector and also serving to seal said mechanical locking means without requiring separate sealing means, said mechanical locking means being accessible solely through said opening through which said pin is engaged in said connector.

2. A sealed electrical connector, especially for use with an implantable cardiac stimulator, comprising an electrically insulated pin having a stripped end, a receptacle receiving said end of said pin, means for conducting electricity from said pin, mechanical means for locking said pin with respect to said receptacle, said receptacle having a smooth hole to receive said pin and an adjacent hole housing said mechanical locking means, and means for sealing the connection between said pin and said receptacle and also sealing said mechanical locking means without requiring separate sealing means, said sealing means comprising a sleeve of elastomeric material having an opening through which said pin is engaged in said connector and a communicating channel through which said mechanical locking means is accessible, said mechanical locking means being accessible solely through said opening through which said pin is engaged in said connector and said communicating channel.

3. A sealed electrical connector, especially for use with an implantable cardiac stimulator, comprising an electrically insulated pin having a stripped end, a receptacle receiving said end of said pin, means for conducting electricity from said pin, said receptacle comprising a cup in which said means for conducting electricity is partially housed and an insert housed in said cup and fixedly secured thereto, mechanical means for locking said pin with respect to said receptacle and means for sealing the connection between said pin and said receptacle, said sealing means having an opening through which said pin is engaged in said connector and also serving to seal said mechanical locking means without requiring separate sealing means, said mechanical locking means being accessible solely through said opening through which said pin is engaged in said connector.

4. A connector according to claim 3, in which the insert has a tapped hole on one axis, a smooth hole on another axis, and a blind hole connecting the other two holes starting from the inner face of the insert and directed towards the base of the cup, the means for conducting electricity being at least partly housed therein.

5. A connector according to claim 4, in which the sealing means is in the form of a sleeve having an inner part housed in the cup adjacent the insert, and provided with a hole formed by the combination of a first hole on said one axis, a second hole on a further axis, the second hole being formed by two sections, namely a first restriction section adjacent the insert, separated from the first-mentioned hole by a projection and a second enlarged section communicating with the first-mentioned hole.

6. A connector according to claim 5, in which the smooth hole and the first restricted section have a larger diameter than that of a stripped end part of the pin.

7. A connector according to claim 5, in which the sealing means also comprise an outer end part, located completely outside the cup, provided with a hole on said further axis, whose diameter in the normal state of slightly smaller than the diameter of an insulation sheath of the pin in the normal state.

8. A connector according to claim 5, in which a slot is provided in the end face of the sleeve in order to facilitate the introduction of the actuating tool.

9. A connector according to claim 5, in which the sleeve also comprises a central part connecting the end parts and provided with a hole which extends the second enlarged section and communicating with the hole on said further axis and a blind hole extending the first hole.

10. A connector according to claim 3, in which the means for conducting electricity comprises and electrical contact member housed in the blind hole and fixed to the free end part of a stem, and being able to be deformed elastically, the contact member being fixed securely to a member itself fixed securely to the cup of the connector and accessible from outside this cup.

11. A connector according to claim 10, in which the mechanical locking means comprise a screw-threaded part co-operating with the tapped hole and being extended by a locking part of frustoconical shape which co-operates with the electrical contact member, and a gripping means permitting actuation of the screw-threaded part.

12. A connector according to claim 11, in which the gripping means is in the form of a blind hole having a cross section whose shape complements that of an actuating tool.

* * * * *